(12) United States Patent
Kong

(10) Patent No.: US 9,784,651 B2
(45) Date of Patent: *Oct. 10, 2017

(54) APPLICATION OF A FLUORINE-CONTAINING POLYMER IN PREPARATION OF TRANSPARENT FROZEN SOIL

(71) Applicant: Hohai University, Nanjing, Jiangsu (CN)

(72) Inventor: Gangqiang Kong, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 77 days.

This patent is subject to a terminal disclaimer.

(21) Appl. No.: 14/763,528

(22) PCT Filed: May 27, 2014

(86) PCT No.: PCT/CN2014/078494
§ 371 (c)(1),
(2) Date: Jul. 27, 2015

(87) PCT Pub. No.: WO2015/165137
PCT Pub. Date: Nov. 5, 2015

(65) Prior Publication Data
US 2016/0244545 A1 Aug. 25, 2016

(30) Foreign Application Priority Data

Apr. 30, 2014 (CN) ............ 2014 1 0177674
Apr. 30, 2014 (CN) ............ 2014 1 0179108
Apr. 30, 2014 (CN) ............ 2014 1 0180405

(51) Int. Cl.
| | |
|---|---|
| G01N 1/28 | (2006.01) |
| G01N 33/22 | (2006.01) |
| C08F 214/26 | (2006.01) |
| C08F 224/00 | (2006.01) |
| H04N 7/18 | (2006.01) |
| G01N 1/42 | (2006.01) |
| G01N 1/38 | (2006.01) |
| G01N 33/24 | (2006.01) |
| F42D 3/00 | (2006.01) |

(52) U.S. Cl.
CPC ............ *G01N 1/28* (2013.01); *C08F 214/262* (2013.01); *C08F 224/00* (2013.01); *F42D 3/00* (2013.01); *G01N 1/2806* (2013.01); *G01N 1/38* (2013.01); *G01N 1/42* (2013.01); *G01N 33/227* (2013.01); *G01N 33/24* (2013.01); *H04N 7/181* (2013.01)

(58) Field of Classification Search
CPC ...... G01N 1/28; G01N 33/227; G01N 1/2806; G01N 1/42; G01N 1/38; G01N 33/24; C08F 214/262; C08F 224/00; H04N 7/181; F42D 3/00
See application file for complete search history.

(56) References Cited

U.S. PATENT DOCUMENTS

| | | | |
|---|---|---|---|
| 2006/0148971 A1* | 7/2006 | Jing ............ | C08J 3/005 524/520 |
| 2016/0244547 A1* | 8/2016 | Jagannathan ...... | B01J 3/008 |

FOREIGN PATENT DOCUMENTS

| | | | |
|---|---|---|---|
| CN | 102230856 | | 11/2011 |
| JP | 2009073954 A | * | 4/2009 |
| SU | 1157452 | | 5/1985 |

OTHER PUBLICATIONS

Derwent Abstract of CN 102230856 A, 2013.*
International Search Report and Written Opinion of PCT/CN2014/078494 dated Feb. 4, 2015, 11 pages.
Allersma, H. G. B., 1982, "Photo-Elastic Stress Analysis and Strains in Simple Shear," Proceedings, IUTAM Symposium on Deformation and Failure of Granular Materials, Delft, edited by P. A. Vermeer and H. J. Luger, pp. 345-353.
Iskander, M., Lai, J., Oswald, C., and Mainnheimer, R., 1994, "Development of a Transparent Material to Model the Geotechnical Properties of Soils," Geotech. Test. J., vol. 17(4), pp. 425-433.
Iskander, M., Liu, J., and Sadek, S., 2002a, "Optical Measurement of Deformation Using Transparent Silica Gel to Model Sand," Int. J. Phys. Modell. Geotech., vol. 2(4), pp. 27-40.
Iskander, M., Liu, J., and Sadek, S., 2002b, "Transparent Amorphous Silica to Model clay," J. Geotech. Geoenviron. Eng., vol. 128(3), pp. 262-273.
Liu, J. Y., Iskander, M., and Sadek, S., 2003, "Consolidation and Permeability of Transparent Amorphous Silica," Geotech. Test. J., vol. 26(4), pp. 390-401.
Wu Mingxi, 2006, Study on synthetic transparent soil and its triaxial test [D], Magisterial thesis, Dalian, Dalian University of Technology, pp. 18-21 (w/ English Abstract).
Sui Wanghua, Gao Yue. Status and prospect of transparent soil experimental technique[J], Journal of China Coal Society, 36(4): 577-582.
Cao, Z. H., Liu, J. Y., and Liu, H. L., 2011, "Transparent Fused Silica to Model Natural Sand," Pan-Am CGS Geotechnical Conference.

(Continued)

Primary Examiner — Nicole M Buie-Hatcher
(74) Attorney, Agent, or Firm — Rankin, Hill & Clark LLP

(57) ABSTRACT

Particles of a fluorine-containing polymer used as a transparent solid material in an artificial transparent frozen soil is provided. The fluorine-containing polymer is poly[4,5-difluoro-2,2bis(trifluoromethyl)-1,3-dioxole-co-tetrafluoroethylene], with a refractive index of 1.31 and a density of 2.1-2.3 g/cm$^3$. The particles have a particle diameter of 0.25-2.0 mm or a particle diameter 0.074 mm, and have irregular shapes. When particles of the fluorine-containing polymer are used as a transparent solid material for preparing a transparent frozen soil, the prepared transparent frozen soil has high transparency, low price, no toxicity and no harm, good similarity with the properties of a natural frozen soil body, can substitute natural frozen soil, is used for simulating complicated geological conditions, and is effectively used in model tests in geotechnical engineering.

10 Claims, No Drawings

(56) References Cited

OTHER PUBLICATIONS

Ezzein, F. M., and Bathurst, R. J., 2011, "A Transparent Sand for Geotechnical Laboratory Modeling," Geotech. Test. J., vol. 34(6), pp. 590-601.

Guzman, I. L., Iskander, M., Suescun-Florez, E., and Omidvar, M., 2013, "A Transparent Aqueous-Saturated Sand Surrogate for Use in Physical Modeling," Acta Geotechnica, published on line, Jul. 2013.

\* cited by examiner

APPLICATION OF A FLUORINE-CONTAINING POLYMER IN PREPARATION OF TRANSPARENT FROZEN SOIL

TECHNICAL FIELD

The present invention relates to the application of a fluorine-containing polymer in the preparation of a transparent frozen soil.

BACKGROUND ART

In model tests in the aspect of the geotechnical engineering, the studies on the internal transformation law and mechanism of soil bodies are of great significance on the research of the problem inherence of the geotechnical engineering. Particularly, the area of perennial frozen soil, seasonal frozen soil and temporary frozen soil regions on earth approximately accounts for 50% of the land area, wherein the distribution area of perennial frozen soil is 35,000,000 $km^2$, approximately accounting for 20% of the land area. And there are great difference between the engineering characteristics of frozen soil and those of conventional soil, hence, it is very implant to develop the study on the engineering characteristics of frozen soil and the characteristics of a constructed object in a frozen soil region.

The patent with the patent number of 201110074794.2, and the invention title of A Method for Preparing High-Water Content Frozen Soil Sample disclosed a technical method for preparing a high-water content frozen soil sample by utilizing conventional equipment, the method could prepare a high-ice content frozen soil sample according to actually required dimensions, and based on the prepared frozen soil sample, a soil testing instrument was used to test the engineering characteristics of the frozen soil.

However, conventional soil body deformation measurement method is to embed a series of sensors inside the soil body, and obtain the displacements of some discrete points, the sensors are easily subjected to the effect due to the disturbance of the external environment, the measurement result often are not accurate, and the whole displacement field in continuous deformation inside the soil body can not be presented as well; and the embedment of the sensors also generate disturbance on the real soil body environment. Modern digital image technologies are only limited to measure the macroscopic or boundary deformation of the soil body as well, and can not realize the visualization of the internal deformation of the soil body; and although X-ray, γ-ray, computer assisted tomographic scanning (CAT scanning) and magnetic resonance imaging technology (MRI) can be used for measuring the continuous deformation inside the soil body, and expensive expenses limit wide application of these technologies. Artificial synthesis of transparent soil in combination with optical observation and image processing techniques is utilized to realize the visualization of the internal deformation of the soil body, with low expense, and simple operation. However its precondition is to obtain an artificially synthesized transparent soil with high transparency, and the properties similar to the natural soil body. At present, different materials were adopted to prepare transparent soil, and some achievements were obtained, for example:

document 1: Allersma, H. G B., 1982, "Photo-Elastic Stress Analysis and Strains in Simple Shear," Proceedings, IUTAM Symposium on Deformation and Failure of Granular Materials, Delft, edited by P. A. Vermeer and H. J. Luger, pp. 345-353.

In document 1, in 1982, Allersma put forward that a mixture of a broken glass (with the refractive index of 1.4738) material and a liquid with the same refractive index was used, for preparing a transparent soil.

document 2: Iskander, M., Lai, J., Oswald, C., and Mainnheimer, R., 1994, "Development of a Transparent Material to Model the Geotechnical Properties of Soils," Geotech. Test. J., Vol. 17(4), pp. 425-433.

document 3: Iskander, M., Liu, J., and Sadek, S., 2002a, "Optical Measurement of Deformation Using Transparent Silica Gel to Model Sand," Int. J. Phys. Modell. Geotech., Vol. 2(4), pp. 27-40.

document 4: Iskander, M., Liu, J., and Sadek, S., 2002b, "Transparent Amorphous Silica to Model sand soil," J. Geotech. Geoenviron. Eng., Vol. 128(3), pp. 262-273.

document 5: Liu, J. Y., Iskander, M., and Sadek, S., 2003, "Consolidation and Permeability of Transparent Amorphous Silica," Geotech. Test. J., Vol. 26(4), pp. 390-401.

In documents 2-5, in 1998, and 2002, Iskander et al utilized industrially produced amorphous silica powder or gel (with the refractive index of 1.447) and a pore fluid with corresponding refractive index to prepare an artificially synthesized transparent soil.

document 6: Wu Mingxi, 2006, Study on synthetic transparent soil and its triaxial test [D], Magisterial thesis, Dalian, Dalian University of Technology, pp. 18-21.

document 7: Sui Wanghua, Gao Yue. Status and prospect of transparent soil experimental technique[J], Journal of China Coal Society, 36(4): 577-582.

document 8: Cao, Z. H., Liu, J. Y, and Liu, H. L., 2011, "Transparent Fused Silica to Model Natural Sand," Pan-Am CGS Geotechnical Conference.

document 9: Ezzein, F. M., and Bathurst, R. J., 2011, "A Transparent Sand for Geotechnical Laboratory Modeling," Geotech. Test. J., Vol. 34(6), pp. 590-601.

document 10: Guzman, I. L., Iskander, M., Suescun-Florez, E., and Omidvar, M., 2013, "A Transparent Aqueous-Saturated Sand Surrogate for Use in Physical Modeling," Acta Geotechnica, published on line, July 2013. http://link.springer.com/article/10.1007%2Fs11440-013-0247-2

In documents 6-10, in 2006, 2013, etc., Wu Mingxi et al utilized fused quartz sand (with the refractive index of 1.4585) and a liquid with corresponding refractive index such as mixed oil or a calcium bromide solution to prepare an artificially synthesized transparent soil.

Existing technical data show that, solid particles for preparing transparent soil mainly adopt quartz materials, with the refractive index themselves of the solid particles between 1.44-1.46, and adopt borosilicate glass materials, with the refractive index themselves of the solid particles between 1.46-1.48, which is far higher than the refractive index of water of 1.33 and that of ice of 1.31. Hence, the utilization of existing solid particles for preparing transparent soil is incapable of preparing a saturated transparent frozen soil sample.

The fluorine-containing polymer is Teflon AF 1600 produced by American DuPont Company, with the refractive index of 1.31, and the density of 2.1-2.3 $g/cm^3$; and it has the characteristics of high temperature resistance, low temperature resistance, chemical corrosion resistance, no viscosity, no toxicity, no pollution, high transparency and low refractive index, and also has the characteristics of gas permeability structure, hydrophobicity and chemical inertness, and has good similarity with the properties of the natural soil body. Teflon AF 1600 can be dissolved in fluorine solvents, and can be formed into a film or formed by melting and compression; and at present, it is mainly used in coating and impregnation or made into fibers, and the prepared liquid core also has application in various fields of absorption, fluorescence, Raman spectral analysis, gas sensors and the like. And the application of Teflon AF 1600 in the preparation of transparent frozen soil is yet not reported.

SUMMARY OF THE INVENTION

The objective of the present invention is to provide the application of a fluorine-containing polymer in the preparation of transparent frozen soil, and said fluorine-containing polymer is used as a transparent solid material for the preparation of transparent frozen soil.

In order to realize the above technical objective, the present invention provides the application of a fluorine-containing polymer in the preparation of transparent frozen soil: it is used as a transparent solid material while in the preparation of a transparent frozen soil, said fluorine-containing polymer is particles with the particle diameter of 0.25-2.0 mm, and its particles have irregular shape, and are Teflon AF 1600 produced by American DuPont Company (i.e. poly[4,5-difluoro-2,2bis(trifluoromethyl)-1,3-dioxole-co-tetrafluoroethylene]), with the refractive index of 1.31, and the density of 2.1-2.3 g/cm$^3$, and the prepared transparent frozen soil prepared from the fluorine-containing polymer of the particle diameter can be used for simulating a frozen sand soil.

Steps for the preparation of simulated frozen sand soil from the above fluorine-containing polymer are as follows:

(1) material preparation: the dosages of the fluorine-containing polymer, the cube ice and the colorless pore fluid are calculated according to the test conditions and sample size dimensions; said fluorine-containing polymer is particles with the particle diameter of 0.25-2.0 mm, and is subjected to impurity cleaning and oven dried, and its particles have irregular shape, and are Teflon AF 1600 produced by American DuPont Company (i.e. poly[4,5-difluoro-2,2bis(trifluoromethyl)-1,3-dioxole-co-tetrafluoroethylene]), with the refractive index of 1.31, and the density of 2.1-2.3 g/cm$^3$; said cube ice is obtained by mashing a frozen whole ice block, with the particle diameter of 0.1-0.5 mm; the colorless pore fluid is water; preferably, water adopts purified water; and said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%.

(2) blending: in a −6.0° C. to −8.0° C. cryogenic laboratory, firstly the fluorine-containing polymer and the cube ice are stirred uniformly, and loaded into a mold by 2-3 batches for the preparation of a sample, and compacted layer by layer; then water is added into the mold, and fills gaps between the fluorine-containing polymer particles and the cube ice;

(3) vacuuming: a vacuuming device is utilized to remove bubbles residual inside the sample, so that the sample reaches a fully saturated state; and (4) freezing: the sample is loaded in a −20° C. cryogenic box for freezing for 48 h, so as to prepare a transparent frozen soil simulating saturated frozen sand soil, the physical properties of which are: density of 1.53-2.0 g/cm$^3$, weight density of 15-20 kN/m$^3$, and compactness 20-80%; and the mechanical properties are: internal friction angle of 30°-31°, elasticity modulus of 8-61 MPa, and Poisson ratio of 0.2-0.4.

In order to apply transparent frozen oil in the simulation of frozen clay, a fluorine-containing polymer with the particle size ≤0.074 mm can also be used for the preparation of transparent frozen soil, said fluorine-containing polymer particles have irregular shape, and are Teflon AF 1600 produced by American DuPont Company (i.e. poly[4,5-difluoro-2,2bis(trifluoromethyl)-1,3-dioxole-co-tetrafluoroethylene]), with the refractive index of 1.31, and the density of 2.1-2.3 g/cm$^3$, and the transparent frozen soil prepared from the fluorine-containing polymer of this particle diameter can be used for the simulation of a frozen sand soil.

Particularly, a method for preparing transparent frozen clay from the above fluorine-containing polymer comprises the following steps:

(1) material preparation: the dosages of the fluorine-containing polymer, the cube ice and the colorless pore fluid are calculated according to the test conditions and the sample size dimensions; said fluorine-containing polymer is particles with the particle diameter ≤0.074 mm, and is subjected to impurity cleaning and oven dried, and its particles have irregular shape, and are Teflon AF 1600 produced by American DuPont Company (i.e. poly[4,5-difluoro-2,2bis(trifluoromethyl)-1,3-dioxole-co-tetrafluoroethylene]), with the refractive index of 1.31, and the density of 2.1-2.3 g/cm$^3$; said cube ice is obtained by mashing a frozen whole ice block, with the particle diameter ≤0.074 mm; and the colorless pore fluid is water;

(2) blending: in a −6.0° C. to −8.0° C. cryogenics laboratory, firstly the fluorine-containing polymer and the cube ice are stirred uniformly, and loaded into a mold by 2-3 batches for the preparation of a sample, and compacted layer by layer; then water is added into the mold, and fills gaps between the fluorine-containing polymer particles and the cube ice;

(3) vacuuming: a vacuuming device is utilized to remove bubbles residual inside the sample, so that the sample reaches a fully saturated state;

(4) consolidating: placing the sample in a consolidometer, with the consolidation degree OCR value of 0.8-3; and (5) freezing: the sample is loaded in a −20° C. cryogenic box and frozen for 48 h, so as to prepare a transparent frozen soil simulating saturated frozen sand soil, the physical properties of which are: density of 1.63-2.1 g/cm$^3$, weight density of 16-21 kN/m$^3$, and the consolidation degree OCR value of 0.8-3; and the mechanical properties are: internal friction angle of 19°-22°, cohesioncohesion of 1-3 kPa, elasticity modulus of 5-9 MPa, and Poisson ratio of 0.2-0.3.

When said fluorine-containing polymer of the present invention is used as a transparent solid material for preparing a transparent frozen soil, the prepared transparent frozen soil has high transparency, low price, no toxicity and no harm, good similarity with the properties of natural frozen soil body, can widely substitute natural frozen soil, is used for simulating complicated geological conditions, and is effectively used in model tests in the geotechnical engineering.

PARTICULAR EMBODIMENTS

Example 1

Application of a fluorine-containing polymer in the preparation of a transparent frozen soil: it is used as a transparent solid material while in the preparation of a transparent frozen soil, said fluorine-containing polymer is particles with the particle diameter of 0.25-2.0 mm, and its particles have irregular shape, and are Teflon AF 1600 produced by American DuPont Company, with the refractive index of 1.31, and the density of 2.1-2.3 g/cm$^3$.

A production method for the preparation of a transparent frozen oil from the above fluorine-containing polymer comprises the following steps:

(1) material preparation: the dosages of the fluorine-containing polymer, the cube ice and the colorless pore fluid are calculated according to the test conditions and the sample size dimensions; said fluorine-containing polymer is particles with the particle diameter ≤0.074 mm, and is subjected to impurity cleaning and oven dried, and its particles have irregular shape, and are Teflon AF 1600 produced by American DuPont Company, with the refractive index of 1.31, and the density of 2.1-2.3 g/cm$^3$, said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%; said cube ice is obtained by mashing a frozen whole ice block, with the particle diameter of 0.1-0.5 mm; the colorless pore fluid is water, and in order not to affect the refractive index, said water is purified water;

the dosages of the fluorine-containing polymer, the particle ice and the colorless pore fluid are determined according to test conditions and the sample size dimension;

the sample of the example has the water content of 100.0%, the dry density of 0.55 g/cm$^3$, and the sample size (height of 125.0 mm and diameter of 61.8 mm), the temperature of the cryogenic laboratory is of −6.0° C., the mass of the fluorine-containing polymer particles (the mass of particles=dry density×sample volume) required for preparing a sample is calculated to be 206.0 g, and the total water content (water content of 100.0%, and the mass of the total water content is equal to the mass of particles) is 206.0 g; and since sand soil has the non-frozen water content about 15% when the temperature is at −6.0° C., the mass of purified water added in the preparation process of the sample should be 30.9 g, and the mass of the cube ice is 175.1 g;

(2) blending: in the −6.0° C. cryogenics laboratory, firstly the fluorine-containing polymer particles and the particle ice determined in step (1) are stirred uniformly, loaded into a mold by 2-3 batches for the preparation of a sample, and compacted layer by layer, to the designed compactness of 70%; then water is added into the mold, and fills the gaps between the fluorine-containing polymer particles and the cube ice;

(3) vacuuming: a vacuuming device is utilized to remove bubbles residual inside the sample, so that the sample reaches a fully saturated state; and (4) freezing: the sample is loaded in a −20° C. cryogenic box and frozen for 48 h, so as to prepare a transparent frozen soil simulating saturated frozen clay, the physical properties of which are: density of 1.9 g/cm$^3$, weight density of 19 kN/m$^3$, and compactness of 70%; and the mechanical properties are: internal friction angle of 20°, cohesion of 3 kPa, elasticity modulus of 40 MPa, and Poisson ratio of 0.3.

Said transparent frozen soil of the example can be used for simulating saturated frozen sand soil.

Example 2

The preparation steps are the same as those of the example 1, and the difference is, in step (1), fluorine-containing polymer particles of the density of 2.1 g/cm$^3$ are selected, fluorine-containing polymer particles with the particle diameter greater than or equal to 0.25 mm and smaller than 0.5 mm account for 20%, those with the particle diameter greater than or equal to 0.5 mm and smaller than 1.0 mm account for 30%, those with the particle diameter greater than or equal to 1.0 mm and smaller than 1.5 mm account for 30%, those with the particle diameter greater than or equal to 1.5 mm and smaller than 2.0 mm account for 20%, in terms of weight, the sum is 100%, and they are mixed uniformly;

In step (2), the compactness is controlled at 30%; the physical properties of the transparent frozen soil prepared by the example are: density of 1.82 g/cm$^3$, weight density of 18 kN/m$^3$, and compactness 30%; and the mechanical properties are: internal friction angle of 30°, elasticity modulus of 10 MPa, and Poisson ratio of 0.35.

Said transparent frozen soil of the example can be used for simulating saturated frozen sand soil.

Example 3

Application of a fluorine-containing polymer in the preparation of a transparent frozen soil: it is used as a transparent solid material while in the preparation of a transparent frozen soil, and the preparation of the transparent frozen soil comprises the following steps:

(1) material preparation: the dosages of the fluorine-containing polymer, the cube ice and the colorless pore fluid are calculated according to the test conditions and the sample size dimensions; said fluorine-containing polymer is particles with the particle diameter ≤0.074 mm, and is subjected to impurity cleaning and oven dried, and its particles have irregular shape, and are Teflon AF 1600 produced by American DuPont Company, with the refractive index of 1.31, and the density of 2.1-2.3 g/cm$^3$; said cube ice is obtained by mashing a frozen whole ice block, with the particle diameter ≤0.074 mm; and the colorless pore fluid is water, and in order not to affect the refractive index, said water is purified water.

The test conditions and the sample size dimension and the calculation method of the example are the same as those of example 1.

In the example, the dosages of the fluorine-containing polymer particles, the cube ice and purified water are 206.0 g, 175.1 g and 30.9 g, respectively.

(2) blending: in the −6.0° C. cryogenics laboratory, firstly the fluorine-containing polymer particles and the particle ice determined in step (1) are stirred uniformly, loaded into a mold by 2-3 batches for the preparation of a sample, and compacted layer by layer, to a designed compactness; then water is added into the mold, and fills the gaps between the fluorine-containing polymer particles and the cube ice;

(3) vacuuming: a vacuuming device is utilized to remove bubbles residual inside the sample, so that the sample reaches a fully saturated state; and (4) consolidating: placing the sample in a consolidometer for consolidation, with the consolidation degree OCR value of 1.5; and (4) freezing: the sample is loaded in a −20° C. cryogenic box and frozen for 48 h, so as to prepare a transparent frozen soil simulating saturated frozen clay, the physical properties of which are: density of 1.93 g/cm³, and weight density of 19.1 kN/m³; and the mechanical properties are: internal friction angle of 20°, cohesion of 3 kPa, elasticity modulus of 9 MPa, and Poisson ratio of 0.3. Said transparent frozen soil of the example can be used for simulating saturated frozen sand soil.

Example 4

The preparation steps are the same as those of example 3, and the difference is: in step (1), fluorine-containing polymer particles with the density of 2.1 g/cm³ are selected;

in step (4), the consolidation degree OCR value is 0.8; and the physical properties of the transparent frozen soil prepared by the example are: density of 1.83 g/cm³, and weight density of 18 kN/m³; and the mechanical properties are: internal friction angle of 19°, cohesion of 1 kPa, elasticity modulus of 5.2 MPa, and Poisson ratio of 0.22. Said transparent frozen soil of the example can be used for simulating saturated frozen clay.

When said fluorine-containing polymer of the present invention is used as transparent solid material for preparing a transparent frozen soil, the prepared transparent frozen soil has high transparency, low price, no toxicity and no harm, good similarity with the properties of the natural frozen soil body, can widely substitute natural frozen soil, is used for simulating complicated geological conditions, and is effectively used in model tests in the geotechnical engineering.

The invention claimed is:

1. An artificial transparent frozen soil including a transparent solid material comprising particles of a fluorine-containing polymer, wherein:
   the particles of the fluorine-containing polymer have a particle diameter of 0.25-2.0 mm, and have irregular shapes, and
   the fluorine-containing polymer is poly[4,5-difluoro-2,2bis(trifluoromethyl)-1,3-dioxole-co-tetrafluoroethylene] with a refractive index of 1.31, and a density of 2.1-2.3 g/cm³.

2. The artificial transparent frozen soil according to claim 1, wherein:
   10-50 wt % of the particles of the fluorine-containing polymer have a particle diameter greater than or equal to 0.25 mm and smaller than 0.5 mm,
   10-50 wt % of the particles of the fluorine-containing polymer have a particle diameter greater than or equal to 0.5 mm and smaller than 1.0 mm,
   10-50 wt % of the particles of the fluorine-containing polymer have a particle diameter greater than or equal to 1.0 mm and smaller than 1.5 mm, and
   10-50 wt % of the particles of the fluorine-containing polymer have a particle diameter greater than or equal to 1.5 mm and smaller than 2.0 mm.

3. The artificial transparent frozen soil according to claim 1, further comprising particles of ice and colorless pore fluid.

4. The artificial transparent frozen soil according to claim 3, wherein the particles of ice have a particle diameter of 0.1-0.5 mm, and the colorless pore fluid is purified water.

5. The artificial transparent frozen soil according to claim 3, wherein the mass of the particles of the fluorine-containing polymer is equal to the combined mass of the particles of ice and the colorless pore fluid.

6. The artificial transparent frozen soil according to claim 3, having a density of 1.53-2.0 g/cm³, a weight density of 15-20 kN/m³, a compactness of 20-80%, an internal friction angle of 30°-31°, an elastic modulus of 8-61 MPa, and a Poisson ratio of 0.2-0.4.

7. An artificial transparent frozen soil including particles of ice, colorless pore fluid, and a transparent solid material comprising particles of a fluorine-containing polymer, wherein:
   the particles of the fluorine-containing polymer have a particle diameter 0.074 mm, and have irregular shapes, and
   the fluorine-containing polymer is poly[4,5-difluoro-2,2bis(trifluoromethyl)-1,3-dioxole-co-tetrafluoroethylene] with a refractive index of 1.31, and a density of 2.1-2.3 g/cm³.

8. The artificial transparent frozen soil according to claim 7, wherein the particles of ice have a particle diameter ≤0.074 mm, and the colorless pore fluid is purified water.

9. The artificial transparent frozen soil according to claim 7, wherein the mass of the particles of the fluorine-containing polymer is equal to the combined mass of the particles of ice and colorless pore fluid.

10. The artificial transparent frozen soil according to claim 7, having a density of 1.63-2.1 g/cm³, a weight density of 16-21 kN/m³, a consolidation degree with an OCR of 0.8-3, an internal friction angle of 19°-22°, a cohesion of 1-3 kPa, an elastic modulus of 5-9 MPa, and a Poisson ratio of 0.2-0.3.

* * * * *